United States Patent
Kiefer et al.

(10) Patent No.: US 6,659,104 B2
(45) Date of Patent: Dec. 9, 2003

(54) CERVICAL SPINE RESTRAINT AND SPINE BOARD EQUIPPED WITH SAME

(75) Inventors: Adolph Kiefer, Wadsworth, IL (US); Shelley Kiefer, Wadsworth, IL (US)

(73) Assignee: Adolph Kiefer & Associates, Inc., Zion, IL (US)

( * ) Notice: Subject to any disclaimer, the term of this patent is extended or adjusted under 35 U.S.C. 154(b) by 63 days.

(21) Appl. No.: 10/047,238

(22) Filed: Jan. 14, 2002

(65) Prior Publication Data

US 2003/0131854 A1 Jul. 17, 2003

(51) Int. Cl.[7] ................................................... A61F 5/37
(52) U.S. Cl. ........................................... 128/870; 5/637
(58) Field of Search ................................. 128/846, 869, 128/870; 5/624, 625, 626, 637

(56) References Cited

U.S. PATENT DOCUMENTS

| | | |
|---|---|---|
| 2,141,100 A | 12/1938 | Warden |
| 3,707,734 A | 1/1973 | Matthews |
| 4,473,912 A | 10/1984 | Scheidel et al. |
| 4,528,981 A | 7/1985 | Behar |
| 4,571,757 A | 2/1986 | Zolecki |
| 4,979,520 A * | 12/1990 | Boone ........................ 128/820 |
| 5,243,639 A | 9/1993 | Johnson |
| 5,414,883 A | 5/1995 | Fangrow, Jr. |
| 5,435,323 A | 7/1995 | Rudy |
| 5,515,869 A | 5/1996 | Powell et al. |
| 5,568,662 A | 10/1996 | Gougelet |
| 5,657,766 A * | 8/1997 | Durham ......................... 5/637 |
| 5,771,513 A | 6/1998 | Kirchgeorg et al. |
| 6,223,749 B1 | 5/2001 | Beaty |

OTHER PUBLICATIONS

Adolph Kiefer & Associates, Inc., Zion Illinois—p. 15 of undated catalog—admitted prior art.

* cited by examiner

Primary Examiner—Michael A. Brown
(74) Attorney, Agent, or Firm—Wood, Phillips, Katz, Clark & Mortimer

(57) ABSTRACT

A spine board is equipped with a cervical spine restraint comprising a lower pad, which is adapted to overlie a portion of the spine board and which has a central portion and two lateral portions, and further comprising two lateral pads, each of which is attached to one of the lateral portions. The lower pad has a positionable pad, which is hinged to the central portion of the lower pad and which is positionable in a position wherein the positionable pad overlies the central portion of the lower pad and a position wherein the positionable pad overlies a portion of the spine board but does not overlie the central portion of the lower pad. Straps attached to the lower pad are adapted to be deployed around the lateral pads and to be attached detachably to one another so as to restrain a patient's head on the central portion of the lower pad if the positionable pad does not overlie the central portion thereof, or on the positionable pad if the positionable pad overlies the central portion thereof, and between the lateral pads. The lateral pads having grooves to guide the straps when deployed around the lateral pads.

7 Claims, 3 Drawing Sheets

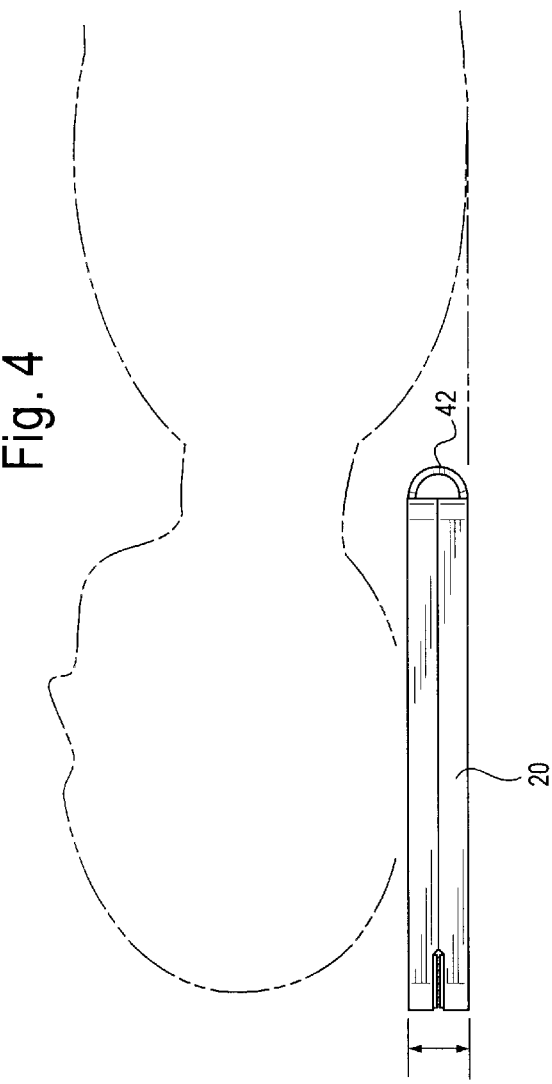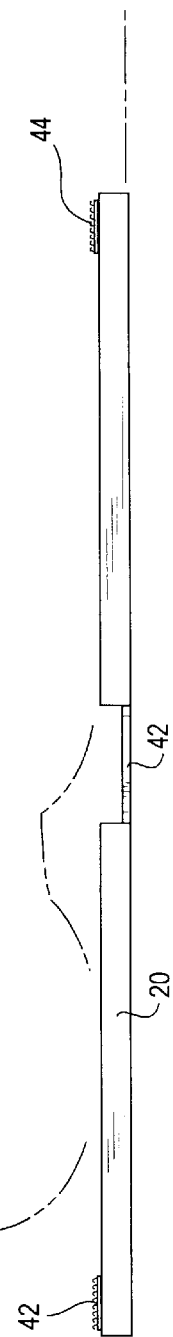

CERVICAL SPINE RESTRAINT AND SPINE BOARD EQUIPPED WITH SAME

TECHNICAL FIELD OF THE INVENTION

This invention pertains to a cervical spine restraint for a spine board, which may be also called a rescue board or a back board, and to a spine board equipped with the cervical spine restraint. The cervical spine restraint is adjustable in a novel manner.

BACKGROUND OF THE INVENTION

A human spine comprises twenty-four vertebrae, which are grouped into three groups, in what are known as the cervical spine, the thoracic spine, and the lumbar spine. Cervical spine injuries, in the neck region, can be quite significant, particularly but not exclusively if they have resulted from motor vehicle collisions, swimming-related causes, or other sports-related causes.

Commonly, the initial care of a person who has been found to have suffered a cervical spine injury, or who may have suffered a cervical spine injury, involves restraining the cervical spine of the person on a spine board, which may be also called a rescue board or a back board, via a cervical spine restraint, which may be also called a head or neck restraint or a head or neck immobilizer. Examples of spine boards, some equipped with cervical spine restraints, are found in prior patents including U.S. Pat. No. 2,141,100, No. 3,707,734, No. 473,912, No. 4,528,981, No. 5,243,639, No. 5,414,883, No. 5,435,323, No. 5,515,869, No. 5,568,662, No. 5,771,513, and No. 6,223,749.

A cervical spine restraint of a type known heretofore comprises a lower pad, which is adapted to overlie a portion of a spine board and which has a central portion and two lateral portions, and further comprising two lateral pads, each of which is attached to one of the lateral portions of the lower pad. Each pad has a core, which is molded from a resilient, polymeric material, and each pad has a vinyl-dipped exterior. The lateral pads, which may be also called side pads or side or lateral blocks, are attached to the lateral portions via hook-and-loop fasteners, which enable the lateral pads to be adjustably positioned on the lateral portions of the lower pad. Straps are attached to the lower pad so as to be deployable around the lateral pads so as to restrain a patient's head on the central portion of the lower pad, between the lateral pads.

When a cervical spine restraint of the type noted above is used, the head of an injured person is rested on the central portion of the lower pad, between the lateral pads, which are positioned to restrain the person's head. Thereupon, the straps attached to the lower pad are deployed around the lateral pads so as to restrain the person's head on the central portion of the lower pad, between the lateral pads. Cervical spine restraints of the type noted above are available commercially from Adolph Kiefer & Associates, Inc. of Zion, Ill., under its "Kiefer Universal Head Immobilizer" trade designation.

SUMMARY OF THE INVENTION

According to a first aspect of this invention, this invention provides, for a spine board, a cervical spine restraint comprising a lower pad, which is adapted to overlie a portion of the spine board and which has a central portion and two lateral portions, and further comprising two lateral pads, each of which is attached to one of the lateral portions. This invention provides that the cervical spine restraint further comprises a positionable pad, which is positionable in a position where the positionable pad overlies the central portion of the lower pad and in positions where the positionable pad does not overlie the central portion of the lower pad. Preferably, the positionable pad is hinged to one of the other pads. In a preferred embodiment, the positionable pad is hinged to the central portion of the lower pad.

In a preferred embodiment, in which the cervical spine restraint further comprises straps attached to the lower pad and adapted to be deployed around the lateral pads so as to restrain a patient's head on the central portion of the lower pad if the positionable pad does not overlie the central portion thereof, or on the positionable pad if the positionable pad overlies the central portion thereof, and between the lateral pads, the lateral pads has grooves to guide the straps when deployed around the lateral pads.

When the positionable pad overlies the central portion of the lower pad, a person's head can rest on the overlying portion while upper portions of the person's torso can rest directly on a spine board underlying the lower pad. When the positionable pad does not overlie the central portion of the lower pad but overlies a portion of a spine board underlying the lower pad, a person's head can rest on the central portion of the lower pad while upper portions of the person's torso can rest on the positionable pad. The cervical spine restraint can be thus adjusted so as to accommodate both a person, such as a large adult, for whom elevation of the persons's head may be indicated and a person, such as a small child, for whom elevation of the person's head may be contraindicated. Whether such elevation is indicated or contraindicated for any given person, in any given instance, is a matter to be decided by medical personnel.

BRIEF DESCRIPTION OF THE DRAWINGS

FIG. 4 is a fragmentary, schematic, lateral view of a lower pad of the cervical spine restraint and of a positionable pad of a central portion of the lower pad, as illustrated in one folded position, in which the positionable pad is illustrated in complete lines in FIGS. 1 and 2.

FIG. 5 is a similar view of the lower pad and of the positionable pad, which is illustrated in a different position, in which the positionable pad is illustrated in complete lines in FIG. 3.

DESCRIPTION OF THE ILLUSTRATED EMBODIMENT

Figure 1:
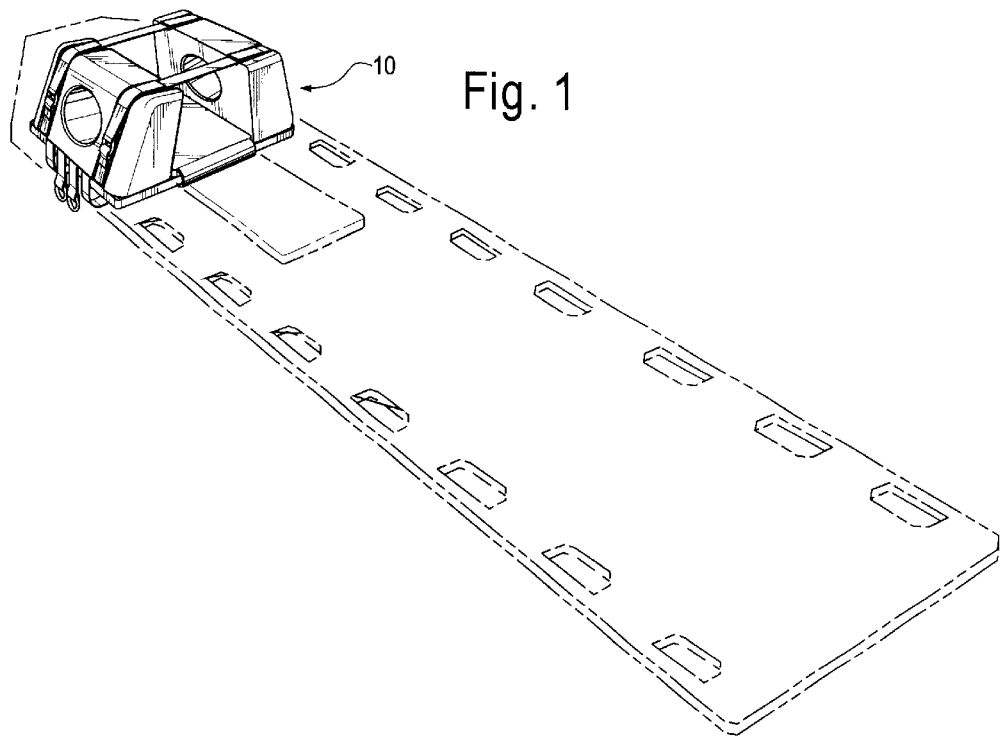
FIG. 1 is a perspective view of a cervical spine restraint embodying this invention, as assembled and as strapped to a spine board, which is illustrated in broken lines.

As illustrated in the drawings, a cervical spine restraint 10 strapped to a spine board, such as the spine board suggested in broken lines in FIG. 1, is used to restrain the cervical spine of an injured person lying on the spine board, by restraining the person's head. Desirably, all materials of the cervical spine restraint 10 are transparent to X-rays, as well as all materials of the spine board. Because of this invention, as described below, the cervical spine restraint 10 is adjustable in an novel manner.

The cervical spine restraint 10 comprises a lower pad 20 and two lateral pads 30, which may be also called side pads or side or lateral blocks. Each of these pads is molded from a polymeric cushioning material, such as polyvinyl chloride (PVC) foam. The lower pad 20 has a central portion 22 and two lateral portions 24. Each of the lateral pads 30 is attached detachably to one of the lateral portions 24 of the lower pad 20.

Preferably, as illustrated, the lateral pads 30 are attached to the lateral portions 22 of the lower pad 20 via hook-and-loop (e.g. Velcro™) fasteners, which comprise loop-faced panels 26 mounted adhesively to generally flat, upper surfaces of the lateral portions 24 of the lower pad 20 and which comprise hook-faced panels 28 mounted adhesively to generally flat, lower surfaces of the lateral pads 30. The hook-and-loop fasteners enable the lateral pads 30 to be adjustably positioned on the lateral portions 24 of the lower pad 20. Two straps 32 attached adhesively to the lateral portions 24 of the lower pad 20, between the loop-faced panels 26 and the upper surfaces mounting the loop-faced panels 26, and provided with associated fastening means are used to strap the cervical spine restraint 10 to a spine board, in a known manner outside the scope of this invention. Two straps 34 attached similarly to the lateral portions 24 of the lower pad 20, between the loop-faced panels 26 and the upper surfaces mounting the loop-faced panels 26, and provided with associated fastening means are deployable around the lateral pads 30, which are molded so as to have grooves 36 to guide the straps 34, so as to restrain a patient's head on the central portion 22 of the lower pad 20, between the lateral pads 30. The straps 32, 34, and associated fastening means are similar to known straps and associated fastening means.

Figure 2:
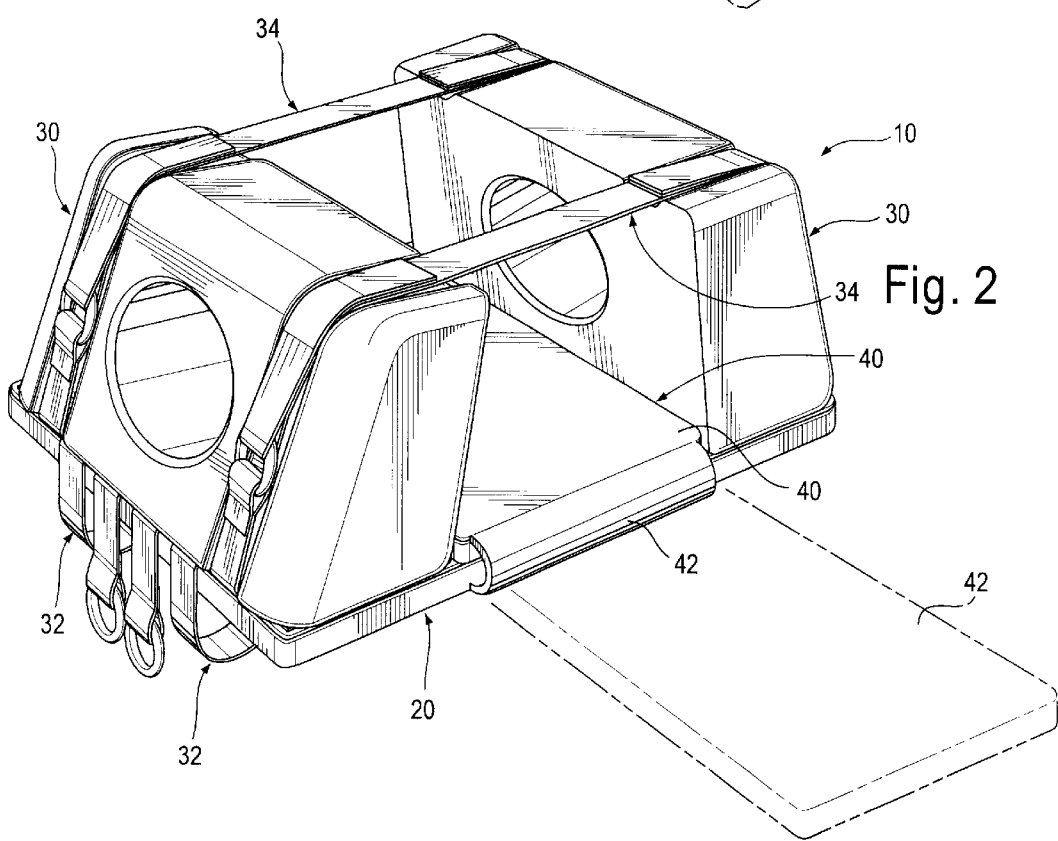
FIG. 2, on a larger scale, is a perspective view of the cervical spine restraint, as assembled, apart from a spine board.
Figure 3:
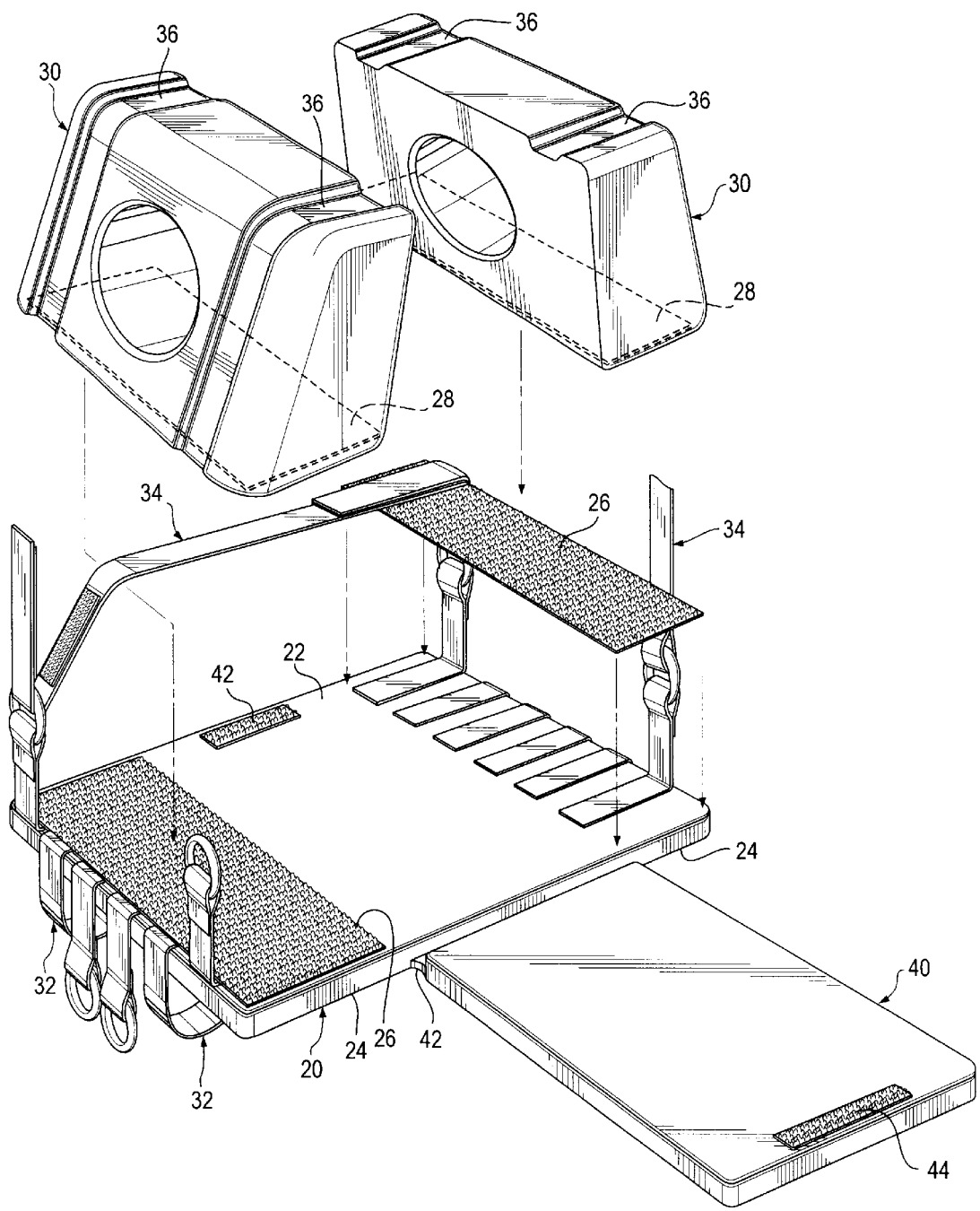
FIG. 3, on a similar scale, is a partly exploded, perspective view of the cervical spine restraint, apart from the spine board.

The cervical spine restraint 10 further comprises a positionable pad 40, which is molded from the polymeric cushioning material used to mold the lower pad 20 and the lateral pads 30. The lower pad 20 and the positionable pad 40 are molded unitarily so that the positionable pad 40 is connected to the central portion 22 of the foldable pad 20 via a unitarily molded, laterally extending hinge 42, whereby the positionable pad 40 is positionable in a position (see FIGS. 2 and 4) where the positionable pad 40 overlies the central portion 22 of the lower pad 20 and in a position (see FIGS. 3 and 5) where the positionable pad 40 does not overlie the central portion 22 of the lower pad 20 but overlies a portion of a spine board underlying the lower pad 20, as well as in intermediate positions where the positionable pad does not overlie either the central portion 22 of the lower pad 20 or a portion of the spine board. Hook-and-loop (e.g. Velcro™) fasteners, which comprise a loop-faced strip 42 mounted adhesively on the upper surface of the central portion 22 of the lower pad 20 and a hook-faced strip 44 mounted adhesively on whichever surface of the positionable pad 40 becomes the lower surface of the positionable pad 40 when overlying the central portion 22 of the lower pad 20, are used to attach the positionable pad 40 detachably to the central portion 22 of the lower pad 20 when the positionable pad 40 overlies the central portion 22 thereof.

A suggested in FIG. 4, when the positionable pad 40 overlies the central portion of the lower pad, a person's head can rest on the overlying portion while upper portions of the person's torso can rest directly on a spine board underlying the lower pad 20. When the positionable pad 40 does not overlie the central portion 22 of the lower pad 20 but overlies a portion of a spine board underlying the lower pad 20, a person's head can rest on the central portion 22 of the lower pad 20 while upper portions of the person's torso can rest on the positionable pad 40. The cervical spine restraint 10 can be thus adjusted so as to accommodate both a person, such as a large adult, for whom elevation of the persons's head may be indicated and a person, such as a small child, for whom elevation of the person's head may be contraindicated.

What is claimed is:

1. For a spine board, a cervical spine restraint comprising a lower pad, which is adapted to overlie a portion of the spine board and which has a central portion and two lateral portions, further comprising two lateral pads, each of which is attached to one of the lateral portions, and further comprising a positionable pad, which is positionable in a position where the positionable pad overlies the central portion of the lower pad and in positions where the positionable pad does not overlie the central portion of the lower pad.

2. The cervical spine restraint of claim 1 further comprising straps attached to the lower pad and adapted to be deployed around the lateral pads and to be attached detachably to one another so as to restrain a patient's head on the central portion of the lower pad if the positionable pad does nor overlie the central portion thereof, or on the positionable pad if the positionable pad overlies the central portion thereof, and between the lateral pads, the lateral pads having grooves to guide the straps when deployed around the lateral pads.

3. For a spine board, a cervical spine restraint comprising a lower pad, which is adapted to overlie a portion of the spine board and which has a central portion and two lateral portions, further comprising two lateral pads, each of which is attached to one of the lateral portions, and further comprising a positionable pad, which is hinged to one of the lower and lateral pads and which is positionable in a position wherein the positionable pad overlies the central portion of the lower pad and in positions wherein the positionable pad does not overlie the central portion of the lower pad.

4. The cervical spine restraint of claim 3 further comprising straps attached to the lower pad and adapted to be deployed around the lateral pads and to be attached detachably to one another so as to restrain a patient's head on the central portion of the lower pad if the positionable pad does not overlie the central portion thereof, or on the positionable pad if the positionable pad overlies the central portion thereof, and between the lateral pads, the lateral pads having grooves to guide the straps when deployed around the lateral pads.

5. For a spine board, a cervical spine restraint comprising a lower pad, which is adapted to overlie a portion of the spine board and which has a central portion and two lateral portions, further comprising two lateral pads, each of which is attached to one of the lateral portions, and further comprising a positionable pad, which is hinged to the lower pad and which is positionable in a position wherein the positionable pad overlies the central portion of the lower pad and in positions wherein the positionable pad does not overlie the central portion of the lower pad.

6. The cervical spine restraint of claim 5 further comprising straps attached to the lower pad and adapted to be deployed wound the lateral pads and to be attached detachably to one another so as to restrain a patient's head on the central portion of the lower pad if the positionable pad does not overlie the central portion thereof, or on the positionable pad if the positionable pad overlies the central portion thereof, and between the lateral pads, the lateral pads having grooves to guide the straps when deployed around the lateral pads.

7. A spine board equipped with the cervical spine restraint of any one of claims 1 through 6 wherein the positionable pad is positionable in a position wherein the positionable pad overlies a portion of the spine board but does not overlie the central portion of the lower pad.

* * * * *